United States Patent
Kullik et al.

(10) Patent No.: US 10,984,908 B2
(45) Date of Patent: Apr. 20, 2021

(54) MEDICAL DEVICE AND METHOD FOR OPERATING A MEDICAL DEVICE

(71) Applicant: Drägerwerk AG & Co. KGaA, Lübeck (DE)

(72) Inventors: Götz Kullik, Lübeck (DE); Stefan Schlichting, Lübeck (DE); Alexander Loose, Reinfeld (DE); Tim Weinmann, Aichtal (DE); Hinrich Althoff, Hamburg (DE)

(73) Assignee: Drägerwerk AG & Co. KGaA, Lübeck (DE)

( * ) Notice: Subject to any disclaimer, the term of this patent is extended or adjusted under 35 U.S.C. 154(b) by 336 days.

(21) Appl. No.: 15/848,227

(22) Filed: Dec. 20, 2017

(65) Prior Publication Data

US 2018/0182487 A1 Jun. 28, 2018

(30) Foreign Application Priority Data

Dec. 22, 2016 (DE) ...................... 10 2016 015 368.7

(51) Int. Cl.
*H04L 29/06* (2006.01)
*G16H 40/67* (2018.01)
(Continued)

(52) U.S. Cl.
CPC ........... *G16H 40/67* (2018.01); *A61B 5/4836* (2013.01); *A61B 5/4839* (2013.01);
(Continued)

(58) Field of Classification Search
CPC .... G16H 40/67; A61B 5/4836; A61B 5/4839; A61B 5/0816; A61B 5/087; H04L 9/14;
(Continued)

(56) References Cited

U.S. PATENT DOCUMENTS 5,682,878 A * 11/1997 Ogden ................ A61M 16/022
128/204.18
6,807,965 B1 * 10/2004 Hickle ................. A61M 16/01
128/204.23

(Continued)

FOREIGN PATENT DOCUMENTS

DE 10 2011 014 889 A1 9/2012

OTHER PUBLICATIONS

David A. Carts, May 2017, A Review of the Diffie-Hellman Algorithm and its Use in Secure Internet Protocolsw, Global Health, https://web.archive.org/web/20170502120514/https://www.sans.org/reading-room/whitepapers/vpns/review-diffie-hellman-algorithm-secure-internet-protocols-751, pp. 1-9.*

(Continued)

*Primary Examiner* — Jason K Gee
(74) *Attorney, Agent, or Firm* — McGlew and Tuttle, P.C.

(57) ABSTRACT

A medical device includes a network interface, a processor unit, a memory unit, an actuator physiologically acting on a patient and/or a sensor interface detecting a sensor signal indicative of a patient physiological parameter. The network interface receives a sender network identity data message, a sender authorization level and a sender change request to change an actuator operating parameter and/or a predefined alarm detection value. The memory unit provides a predefined minimum authorization level. The processor unit determines an actual authorization of the sender to change the operating parameter and/or to predefine a value on the basis of the sender authorization level and of the predefined minimum authorization level as well as to change the operating parameter as a function of the result of the determination and/or to perform a detection of an alarm generation state as a function of the indicated predefined value and of the sensor signal.

17 Claims, 8 Drawing Sheets

(51) Int. Cl.
- *H04L 9/14* (2006.01)
- *H04L 9/30* (2006.01)
- *H04L 9/32* (2006.01)
- *A61B 5/00* (2006.01)
- *H04W 12/08* (2021.01)
- *H04L 9/08* (2006.01)
- *A61B 5/08* (2006.01)
- *A61M 5/172* (2006.01)
- *A61M 16/00* (2006.01)
- *A61B 5/087* (2006.01)
- *A61M 5/142* (2006.01)

(52) U.S. Cl.
CPC .............. *H04L 9/0841* (2013.01); *H04L 9/14* (2013.01); *H04L 9/30* (2013.01); *H04L 9/3226* (2013.01); *H04L 63/0435* (2013.01); *H04L 63/0442* (2013.01); *H04L 63/105* (2013.01); *H04W 12/08* (2013.01); *A61B 5/087* (2013.01); *A61B 5/0816* (2013.01); *A61M 5/142* (2013.01); *A61M 5/1723* (2013.01); *A61M 16/0003* (2014.02); *A61M 16/0051* (2013.01); *A61M 16/026* (2017.08); *A61M 2205/18* (2013.01); *A61M 2205/3553* (2013.01); *A61M 2205/3584* (2013.01); *A61M 2205/3592* (2013.01); *A61M 2205/52* (2013.01); *G06Q 2220/10* (2013.01); *H04L 2209/88* (2013.01)

(58) Field of Classification Search
CPC ..... H04L 9/30; H04L 9/3226; H04L 63/0435; H04L 63/105; A61M 16/0003; A61M 16/026; A61M 16/0051; A61M 5/1723; A61M 2205/18; A61M 5/14244; G06Q 2220/10; G06F 17/60; G06F 19/00; H16H 40/67

See application file for complete search history.

(56) References Cited

U.S. PATENT DOCUMENTS

| | | | | |
|---|---|---|---|---|
| 6,985,771 B2* | 1/2006 | Fischell | | A61B 5/0006 607/3 |
| 7,978,062 B2* | 7/2011 | LaLonde | | A61N 1/37211 340/539.11 |
| 8,287,454 B2* | 10/2012 | Wolpert | | A61B 5/4839 600/365 |
| 8,763,651 B2* | 7/2014 | Stavsky | | B65B 3/003 141/27 |
| 8,814,798 B2* | 8/2014 | Corbucci | | A61B 5/0205 600/438 |
| 8,977,348 B2* | 3/2015 | Su | | A61B 5/029 600/479 |
| 8,995,655 B2* | 3/2015 | Spalka | | H04L 9/14 380/44 |
| 9,192,712 B2* | 11/2015 | DeBelser | | G16H 20/17 |
| 9,302,066 B2* | 4/2016 | Bertinetti | | E05B 17/2057 |
| 9,314,566 B2* | 4/2016 | Wenger | | A61M 5/14244 |
| 9,852,265 B1* | 12/2017 | Treacy | | G08B 5/222 |
| 9,855,110 B2* | 1/2018 | Bitan | | A61B 90/36 |
| 9,861,817 B2* | 1/2018 | Cho | | A61B 5/0809 |
| 10,255,994 B2* | 4/2019 | Sampath | | G06F 19/3418 |
| 10,325,681 B2* | 6/2019 | Sampath | | G16H 40/20 |
| 10,780,224 B2* | 9/2020 | Handler | | G16H 40/63 |
| 2002/0013538 A1* | 1/2002 | Teller | | A61B 5/6831 600/549 |
| 2002/0046152 A1* | 4/2002 | Kinney | | G06Q 40/025 705/37 |
| 2005/0108057 A1* | 5/2005 | Cohen | | G06Q 50/24 705/3 |
| 2005/0235249 A1* | 10/2005 | Friemelt | | G06Q 10/00 717/102 |
| 2008/0249386 A1* | 10/2008 | Besterman | | A61B 5/0022 600/365 |
| 2009/0037224 A1* | 2/2009 | Raduchel | | G16H 40/20 705/3 |
| 2009/0177769 A1* | 7/2009 | Roberts | | G16H 40/20 709/224 |
| 2010/0280366 A1* | 11/2010 | Arne | | A61B 5/0538 600/425 |
| 2010/0295686 A1* | 11/2010 | Sloan | | G16H 20/17 340/573.1 |
| 2011/0028881 A1* | 2/2011 | Basaglia | | A61M 1/3413 604/4.01 |
| 2011/0148622 A1* | 6/2011 | Judy | | A61B 5/742 340/539.12 |
| 2012/0041279 A1* | 2/2012 | Freeman | | A61M 5/168 600/301 |
| 2014/0207476 A1* | 7/2014 | Fong | | G16H 40/20 705/2 |
| 2015/0039053 A1* | 2/2015 | Kaib | | A61N 1/3993 607/60 |
| 2016/0078191 A1* | 3/2016 | Casimiro | | G16H 50/30 705/3 |
| 2016/0099963 A1* | 4/2016 | Mahaffey | | H04L 63/0227 726/25 |
| 2017/0043089 A1* | 2/2017 | Handler | | H04L 67/12 |
| 2018/0018864 A1* | 1/2018 | Baker | | G08B 21/043 |
| 2019/0320988 A1* | 10/2019 | Ahmed | | A61B 5/002 |
| 2020/0121873 A1* | 4/2020 | Hudson | | A61M 16/024 |

OTHER PUBLICATIONS

David A. Carts (David A. Carts, May 2017, A Review of the Diffie-Hellman Algorithm and its Use in Secure Internet Protocolsw, Global Health, https://web.archive.org/web/20170502120514/https://www.sans.org/reading-room/whitepapers/vpns/review-diffie-hellman-algorithm-secure-internet-protocols-751, pp. 1-9.*

* cited by examiner

FIG. 2a
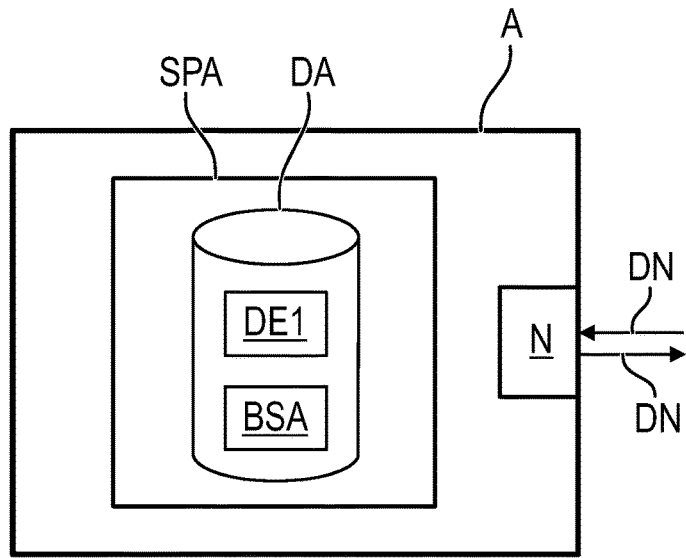
FIG. 2b
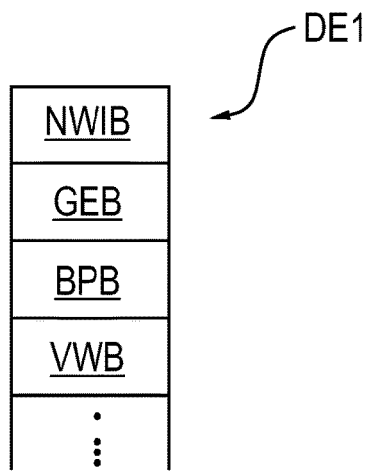
FIG. 2c
| BSA1 | BP1 |
| --- | --- |
| BSA2 | BP2 |
| BSA3 | BP3 |
| ⋮ | ⋮ |
BSA'
FIG. 2d
| BSA11 | VWB1 |
| --- | --- |
| BSA12 | VWB2 |
| ⋮ | ⋮ |
BSA"

| BP1 | MBP1 |
|---|---|
| BP2 | MBP2 |
| BP3 | MBP3 |
| ⋮ | ⋮ |

MB'

| VWB1 | MBV1 |
|---|---|
| VWB2 | MBV2 |
| ⋮ | ⋮ |

MB''

MEDICAL DEVICE AND METHOD FOR OPERATING A MEDICAL DEVICE

CROSS REFERENCE TO RELATED APPLICATIONS

This application claims the benefit of priority under 35 U.S.C. § 119 of German Application 10 2016 015 368.7, filed Dec. 22, 2016, the entire contents of which are incorporated herein by reference.

FIELD OF THE INVENTION

The present invention pertains to a medical device which has an actuator for physiologically acting on a patient connected to the device and/or a medical device with a sensor interface and a sensor of a patient physiological parameter.

BACKGROUND OF THE INVENTION

Medical devices that have an actuator for acting physiologically on a patient connected to the medical device are known from the state of the art. For example, a ventilator (also known as a respirator), which may have a breathing gas delivery unit as an actuator, is an example of such a medical device with an actuator.

So-called patient monitors, which detect by means of a sensor interface a sensor signal, which indicates a physiological parameter, for example, a blood pressure or a heart rate of a patient, are likewise known as medical devices.

A function control of such a medical device with an actuator and/or with a sensor interface is usually carried out via an operating parameter (e.g., predefined pressure, predefined volume flow) or via a predefined value (e.g., a threshold value) relative to an alarm generation function.

For example, a minimum end-expiratory pressure to be reached may be set as an operating parameter in a ventilator as a medical device. Such an operating parameter consequently directly influences the action on the patient and hence the functionality of the medical device.

In a patient monitor, an alarm generation function is controlled, for example, by a physiological parameter derived from the sensor signal being monitored as a function of a predefined value, wherein an alarm generation function is triggered, for example, when the predefined value or threshold value is exceeded by the physiological parameter.

It is consequently common to the above-mentioned medical devices that the patient's safety or the patient's situation is considerably influenced by an operating parameter and/or by a predefined value relative to an alarm generation function.

Current medical devices frequently have a so-called closed architecture, which is closed in itself, and each medical device acts on its own and an operating parameter and/or a predefined value for an alarm generation function is effected by an input by a user directly on the medical device itself.

However, it happens precisely in acute care that a large number of respective individual medical devices are to perform the supply and/or the monitoring of the patient.

The change in an operating parameter of an actuator of a medical device or else of a predefined value relative to an alarm generation function of the medical device consequently represents a setting of a potentially life-threatening parameter of the medical device in respect to the life of the patient.

Potentially life-threatening settings may be, e.g., —a setting of dispensing rates of drugs at a syringe pump, —or the setting of an alarm threshold for an oxygen saturation in the blood on a patient monitor.

In so-called individual medical devices around the patient, many individual operating steps must be performed on the individual medical device for changing the operation mode (for example, a daytime-nighttime switchover) or as a response to an event (for example, silencing of an output alarm signal). Consequently, an operating parameter or a predefined value relative to an alarm generation function must thus be changed directly on the device itself. This is especially disadvantageous, for example, when a patient must be isolated in a room for avoiding infection and the health care staff must enter such an isolation room protected by special clothing for each operating step and then remove the protective clothing. Further, such clothing must be cleaned or disposed of in an orderly manner.

SUMMARY OF THE INVENTION

An object of the present invention is consequently to provide a medical device in which an operating parameter of the actuator and/or a predefined value relative to an alarm generation function of the medical device can be changed and set safely by a user via a network without direct input.

According to the invention, a medical device is provided, which has an actuator for physiologically acting on a patient connected to the device and/or which has a sensor interface for detecting a sensor signal, which indicates a physiological parameter of a patient. The device further has a network interface, a processor unit as well as a memory unit, wherein the network interface is configured to receive at least one data message, which indicates a network identity of the sender of the message, at least one authorization level of the sender as well as a request of the sender to change an operating parameter of the actuator and/or to change a predefined value for an alarm detection. Further, the memory unit is configured to provide a predefined minimum authorization level and wherein the processor unit is furthermore configured to determine an actual authorization of the sender to change the operating parameter and/or to predefine the predefined value on the basis of the authorization level of the sender and of the predefined minimum authorization level as well as to change the operating parameter and/or to detect an alarm generation state as a function of the indicated predefined value and of the sensor signal as a function of the result of the determination.

The medical device according to the invention is advantageous because it is ensured thereby that the setting of vitally important parameters relative to a patient is only possible by network units that also do, indeed, have a necessary authorization. The minimum authorization level as well as the authorization level indicated by the sender can be assigned here by a central authorization management unit, so that a central computer has the control over which network units can perform an adjustment of these vitally important parameters on the medical device. Such a vitally important parameter is consequently, for example, the operating parameter of the actuator or the predefined value relative to the alarm generation state.

A corresponding architecture, in which a flexible combination of medical devices is made possible from a data networking, so that secure and reliable function control is possible, is made possible by means of the proposed functionality of the medical device.

A method for operating a medical device is likewise provided, wherein the medical device has a network interface, a processor unit and a memory unit as well as, furthermore, an actuator for physiologically acting on a patient connected to the device and/or a sensor interface for detecting a sensor signal, which indicates a physiological parameter of a patient. The method further has the steps of—receiving, by means of the network interface, at least one data message, which indicates a network identity of a sender of the message, at least one authorization level of the sender as well as a request on the sender to change an operating parameter of the actuator and/or to change a predefined value for an alarm detection, —providing, by means of the memory unit, a predefined minimum authorization level, —determining, by means of the processor unit, an actual authorization of the sender to change the alarm threshold value on the basis of the authorization level of the sender and of the predefined minimum authorization level, —as well as, furthermore, changing the operating parameter and/or detecting an alarm generation state as a function of the predefined value and of the sensor signal as a function of the result of the determination and by means of the processor unit.

The method for operating the medical device offers the advantages that were mentioned above with reference to the medical device.

The medical device is preferably characterized in that the predefined value is a threshold value and that the processor unit is configured to determine a parameter value of the physiological parameter of the patient on the basis of the sensor signal and further to perform the detection of the alarm generation state as a function of the parameter value and of the threshold value.

This embodiment is advantageous because the change in the threshold value on the medical device is only possible for network computers that have a necessary minimum authorization, and the authorization management can be carried out here by a central computer.

The medical device is preferably characterized in that the predefined value indicates a request on whether or not the detection of the alarm generation state shall be carried out, and that the processor unit is configured to carry out the detection of the alarm generation state as a function of the predefined value.

This embodiment is advantageous because a so-called alarm suppression on the medical device from the outside via a network computer is only possible via network computers that have a necessary minimum authorization. The central authorization management can be controlled by a central network computer in this case as well.

The medical device is preferably characterized in that the data message is an encrypted data message.

This embodiment is advantageous because the medical device can analyze the data message after corresponding decryption, so that an unauthorized third network computer is incapable of changing the data message to change the operating parameter or else to change the predefined value relative to the alarm generation function, because this third network computer does not have the data key for encrypting the data message.

The medical device is preferably characterized in that the processor unit is further configured to exchange handshake messages with the sender via the network interface in order to successfully reach an agreement with the sender on a symmetrical key and to apply the symmetrical key to the data message after successful agreement.

The medical device is preferably characterized in that the memory unit is further configured to provide a private key and a public key, the processor unit being further configured to exchange the handshake messages with the sender on the basis of the private key and public key via the network interface in order to successfully bring about the agreement with the sender about the symmetrical key, and to apply the symmetrical key to the data message after a successful agreement. The handshake messages are preferably so-called SSL or TLS handshake messages.

This embodiment is advantageous because it makes it possible to transmit additional subsequent data messages after a so-called handshake in the keep alive functionality by means of encrypting by a symmetrical key. A symmetrical encryption is faster than a so-called asymmetric encryption from the viewpoint of the amount of computing needed. An especially time-efficient data transmission is proposed here.

The medical device is preferably characterized in that the processor unit is further configured to exchange the handshake messages via the network interface according to the Diffie-Hellman method in order to successfully reach the agreement with the sender about the symmetrical key and to apply the symmetrical key to the data message after successful agreement.

The medical device is preferably characterized in that the processor unit is configured to exchange data messages via the network interface to determine the data transmission quality between the sender and the medical device and further to change the operating parameter and/or to perform the detection of the alarm generation state as a function of the result of the determination and of the determined data transmission quality.

This embodiment is advantageous because by taking the data transmission quality into consideration, it is possible to detect a disturbed data transmission between the sender and the medical device and to make the change in the operating parameter or the detection of the alarm generation state contingent hereon. If the quality of the data transmission is too poor, it is possible that a requested parameter value or a requested predefined value was not transmitted correctly or, for example, it was transmitted too slowly, so that a change in the operating parameter or in the predefined value could be disadvantageous for the patient. Such a disadvantageous situation is therefore prevented from occurring by taking the data transmission quality into consideration.

The medical device is preferably characterized in that the data message further has a time stamp and that the processor unit is configured to change the operating parameter and/or to perform the detection of the alarm generation state as a function of the result of the determination and of the time stamp.

This embodiment is advantageous because the medical device can detect on the basis of the time stamp whether the requested operating parameter value or else the requested predefined value relative to the alarm generation function is indeed also in a chronological relationship that is meaningful for an application in the medical device for the patient.

The present invention will be explained in more detail below on the basis of special embodiments without limitation of the general inventive idea on the basis of the figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 2a is an abstract view of a sender;

FIG. 2b is a view showing data elements that may be stored in a memory unit of a sender;

FIG. 2c is a view showing a preferred embodiment of authorization levels of the sender;

FIG. 2d is a view showing another preferred embodiment of authorization levels of the sender;

DESCRIPTION OF THE PREFERRED EMBODIMENTS

Figure 1A:
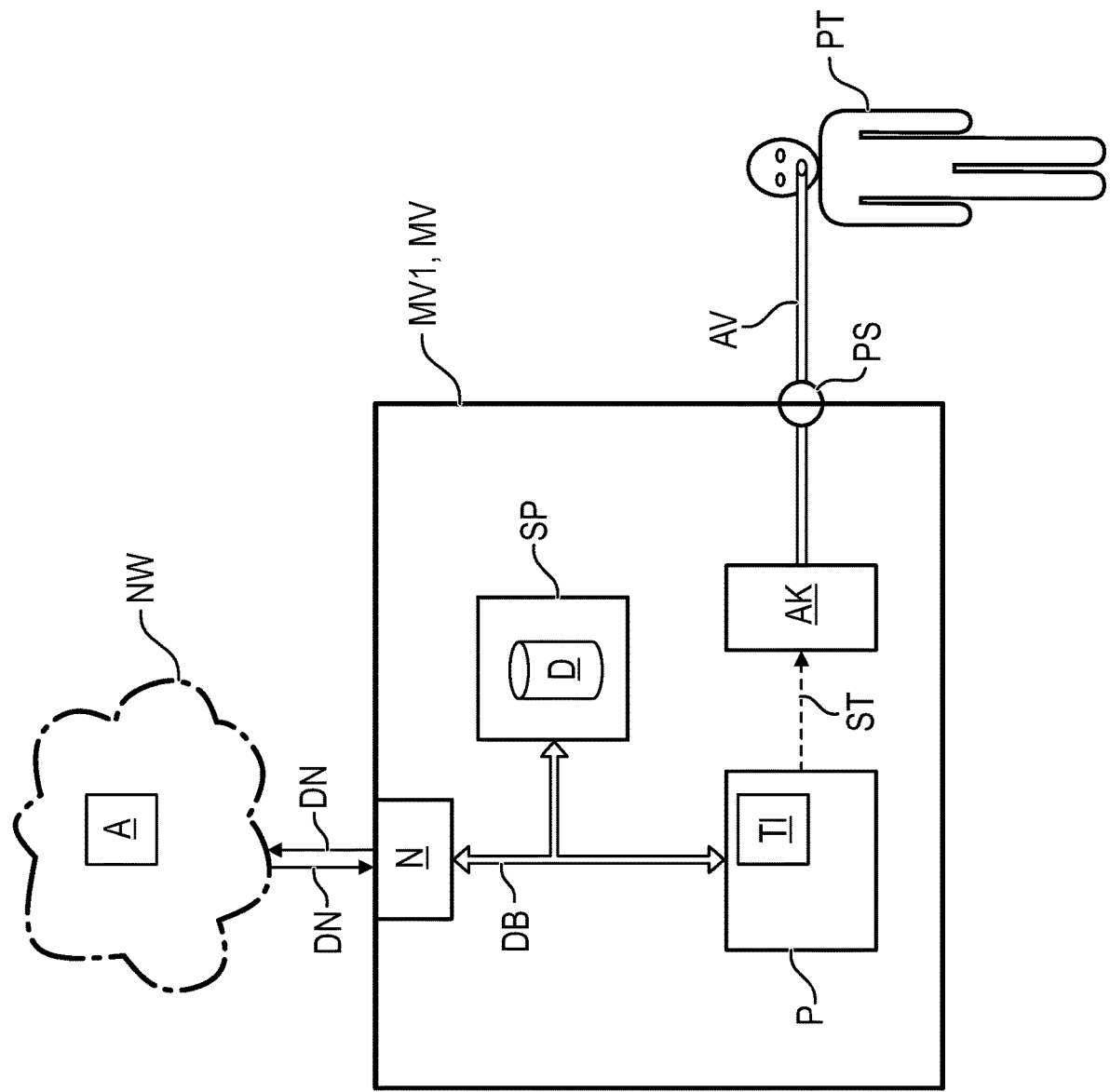
FIG. 1a is a schematic view showing a first preferred embodiment of the medical device.
Figure 1B:
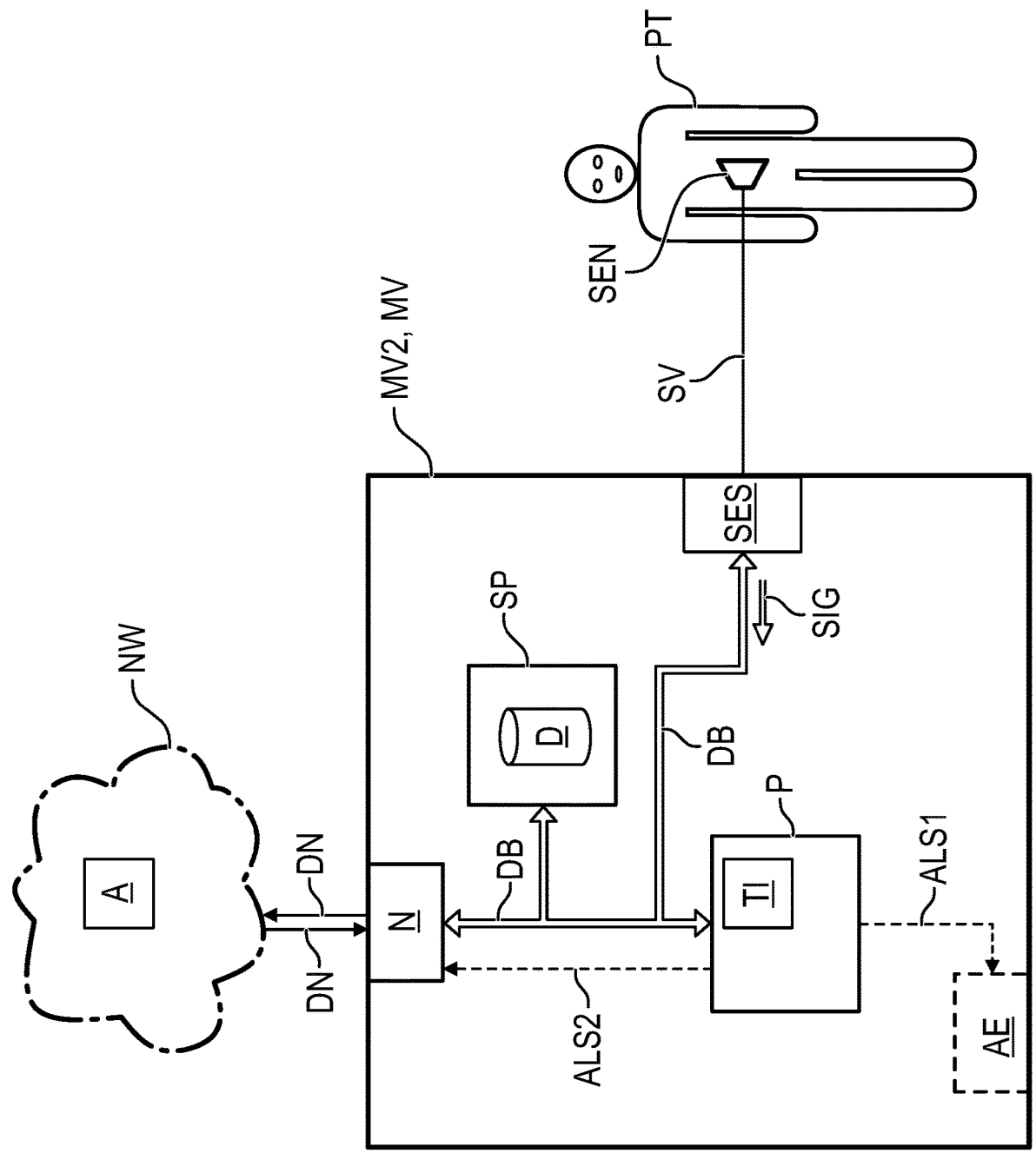
FIG. 1b is a schematic view showing a second preferred embodiment of the medical device.

Referring to the drawings, FIGS. 1a and 1b show respective preferred embodiments of the medical device according to the invention.

FIG. 1a shows a medical device MV1, which has an actuator AK for physiologically acting on a patient PT connected to the device MV1. This action preferably takes place via a patient interface PS, via which the actuator AK is connected to the patient PT via a connecting line AV.

Examples of such a medical device MV1 are, for example, a ventilator, in which a breathing gas delivery unit represents the actuator AK.

As an alternative, that the medical device MV1 is, for example, a so-called syringe pump, in which the actuator AK is a motor or a stepping motor, in order to control the administration of an injection solution via the syringe pump or injection pump in terms of the quantity of injection to the patient PT.

For example, a minimum end-expiratory pressure, a respiration rate or, for example, a pressure stroke (PInsp) is an example of an operating parameter of an actuator AK in case of a medical device MV1 as a ventilator.

For example, a volume rate per unit of time for an injection solution, which is delivered by the stepping motor to the patient PT, may be an example of an operating parameter of an actuator AK in case of a syringe pump or injection pump.

The medical device MV1 has a network interface N, via which the device MV1 exchanges data messages DN with a sender A from a network NW.

The device MV1 further has a memory unit SP, in which data D are stored.

The device MV1 further has a processor unit P, which controls the actuator AK via a control signal ST and uses one or more operating parameters for this. The processor unit P consequently selects the control signal ST for the actuator AK as a function of one or more operating parameters.

The processor unit P preferably has a timer function TI.

The device MV1 further has a memory unit SP.

The memory unit SP, the processor P as well as the network interface N are preferably connected to one another via an internal data bus DB.

FIG. 2a shows for this an abstract view of the sender A, who maintains data DA in a memory unit SPA. The sender A can exchange data messages DN via a corresponding network interface N.

The stored data DA preferably have a data element DE1, which is shown more specifically in FIG. 2b.

The data element DE1 preferably has additional partial data segments, which indicate different pieces of information.

A partial data element NWIB is the network identity of the medical device MV1 from FIG. 1a. The sender A consequently knows the network identity of the medical device MV1.

The data element DE1 further has a partial data element GEB, which indicates the properties or the type or the class of the medical device MV1.

Another partial data element BPB indicates a type of an adjustable operating parameter of the device MV1.

The data element DE1 preferably has a partial data element VWB, which indicates a predefined value type relative to a certain type of an alarm generation function, so that the sender knows which predefined values can be changed or set for which types of alarm generation on the medical device MV1.

FIG. 2a further shows an authorization level BSA of the sender A as part of the data DA in the memory unit SPA of the sender A. This part may be, for example, an individual authorization level, which the sender A has.

This authorization level is decisive for whether the sender A can change an operating parameter on the medical device MV1 from FIG. 1a or whether the medical device MV1 takes into consideration a predefined value relative to an alarm generation function predefined by the user A.

FIGS. 2c and 2d show preferred embodiments BSA' and BSA" of the authorization level BSA of the sender A from FIG. 2a.

FIG. 2c shows a list BSA', which provides different authorization levels BSA1, BSA2, BSA3 for respective operating parameters BP1, BP2, BP3. Consequently, a different authorization level BSA1, BSA2, BSA3 of the sender A from FIG. 2a may be given here for a particular, different operating parameter BP1, BP2, BP3.

This also applies to the authorization level BSA11, BSA12 from FIG. 2d relative to corresponding predefined value types VWB1, VWB2.

Figures 3A, 3B, 3C:
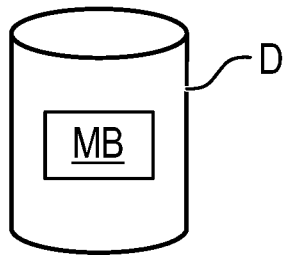
FIG. 3a is an abstract view of a minimum authorization level stored in a memory unit of the medical device.
FIG. 3b is a view showing a preferred embodiment of minimum authorization levels, which may be stored in a memory unit of a medical device.
FIG. 3c is a view showing another preferred embodiment of minimum authorization levels, which may be stored in a memory unit of a medical device.

FIG. 3a shows in an abstract form data D, which are stored in the memory SP of the device MV1 from FIG. 1a. The data D contain a predefined and predetermined minimum authorization level MB.

The minimum authorization level MB is preferably an individual value, which is used to determine whether a sender of a data message is authorized to change an operating parameter or else whether a predefined value predefined by the data message by the sender relative to an alarm generation function shall be used.

FIGS. 3b and 3c show different embodiments MB' as well as MB" of the minimum authorization level MB.

According to FIG. 3b, a list MB' is given, which indicates respective minimum authorization levels MBP1, MBP2, MBP3 for respective operating parameters BP1, BP2, BP3. Consequently, a different minimum authorization level can thus be taken into consideration for different operating parameters.

This also applies to the list MB" from FIG. 3c, according to which different minimum authorization levels MBV1, MBV2 apply to different predefined value types VWB1, VWB2.

Figure 4A:
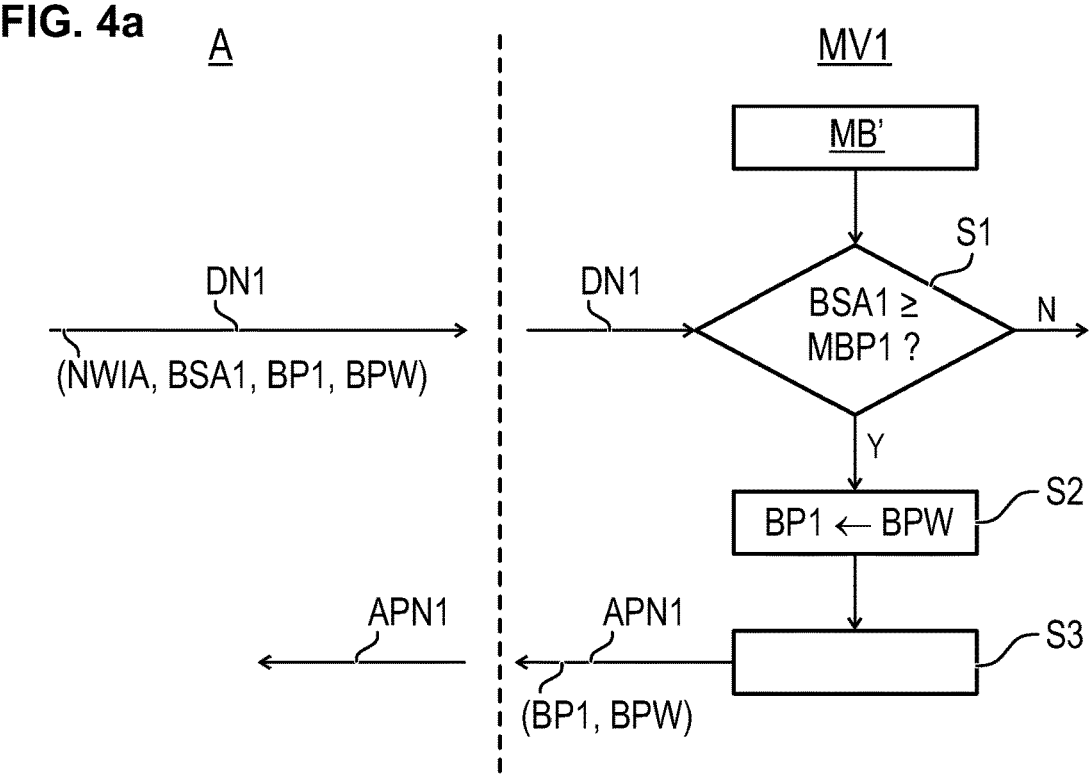
FIG. 4a is a view showing a preferred embodiment of the method according to the present invention.

FIG. 4a shows a preferred embodiment of the method according to the present invention, which corresponds to the medical device MV1 from FIG. 1a.

The sender A sends a directed data message DN1 to the medical device, the data message indicating the network identity NWIA of the sender A. The data message DN1 further indicates an authorization level BSA1 of the sender A. The data message DN1 further indicates a request of the sender A to change an operating parameter BP1. The data message DN1 indicates to this end a requested operating parameter value BPW in this exemplary embodiment.

The device MV1 receives the data message DFN1 and provides a predetermined and predefined minimum authorization level MB1.

In a step S1, the processor unit P of the device MV1 determines whether the sender A is authorized to change the operating parameter BP1. This is carried out on the basis of the authorization level BP1 of the sender A as well as of the predefined minimum authorization level MBP1. If the result of the determination is positive (Y), the process is branched off via a branching to another step S2, in which the operating parameter BP1 is changed to the requested value BPW. If the result of the determination is negative (N), the operating parameter BP1 is not changed.

After a positive result of the determination and after changing the operating parameter BP1, a confirmation message APN1 is sent to the sender A in another step S2. This sending consequently takes place in case of a positive result of the authorization check or a positive result of the determination. The confirmation message APN1 preferably has the operating parameter BP1 as well as the operating parameter value BPW.

FIG. 1b shows an embodiment MV2 of the medical device for the case in which the medical device MV2 has a sensor interface SES for detecting a sensor signal SIG, which indicates a physiological parameter of the patient PT. Via the sensor interface SES, the medical device MV2 is connected by means of a sensor connection SV to the sensor SEN, which is preferably arranged on the body of the patient PT.

The medical device MV2 according to FIG. 1b differs from the medical device MV1 according to FIG. 1a in that the sensor interface SES is likewise connected to the processor unit P via the internal data bus DB. As an additional third embodiment the embodiment of FIG. 1a and the embodiment of FIG. 1b are combined. In particular the patient PT is connected via the patient interface PS and to the actuator AK and processor D of the medical device via the connecting line AV and the sensor SEN at the patient PT is also connected to the sensor interface SES which is connected to the processor P of the medical device by means of a sensor connection SV.

The medical device MV2 is further configured such that the processor unit P is configured to determine an actual authorization of the sender A to predefine a predefined value relative to an alarm generation function on the basis of a received authorization level of the sender A and of a predefined minimum authorization level.

The processor unit P of the device MV2 according to FIG. 1b is further configured to perform a detection of an alarm generation state as a function of the predefined value and the sensor signal SIG.

The data D of the memory unit SP preferably have to this end a list MB", as was described above with reference to FIG. 3c, as minimum authorization data MB from FIG. 3a.

Figure 4B:
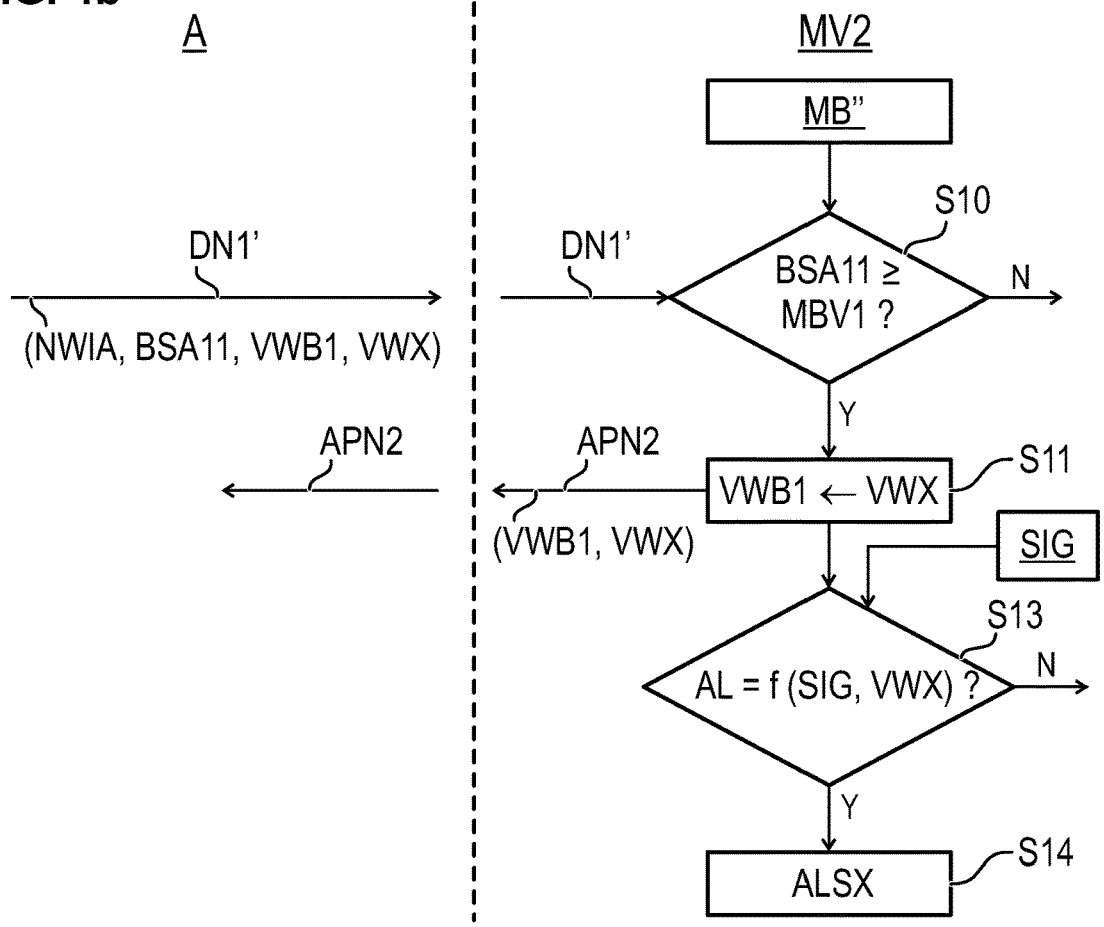
FIG. 4b is a view showing another preferred embodiment of the method according to the present invention.

FIG. 4b shows a preferred embodiment of the method according to the present invention, which is related to the embodiment of the medical device MV2 according to FIG. 1b.

The network identity NWIA of the sender A as well as an authorization level BSA11 of the sender A are indicated in the data message DN1'. Further, a predefined value type VWB1, for which a predefined value VWX is predefined, is indicated.

In a step S10, the processor unit of the medical device MV2 takes into consideration the minimum authorization levels MB" as well as the authorization level BSA11 of the sender A in order to determine whether the sender is authorized to predefine the predefined value VWX for the predefined value type VWB1.

If the result of the determination or the authorization check is positive (Y), a detection of the alarm generation state is performed as a function of the predefined value VWX as well as of the sensor signal SIG from FIG. 1b.

According to FIG. 4b, the process is branched to this end to a step S11, in which the predefined value type VWB1 is set to the preset predefined value type VWX. An authorization message APN2 is preferably sent to the sender A, because the authorization check or the result of the determination was positive. The authorization message APN2 preferably has the predefined value type VWB1 as well as the predefined value VWX or indicates same.

Consequently, the sensor signal SIG is now used in another step S13, and this sensor signal SIG is included together with the predefined value VWX in order to detect the presence of an alarm generation state AL. The alarm generation state AL is consequently a function of the sensor signal SIG and of the predefined value VWX.

If an alarm generation state is present, an alarm generation signal ALSX is outputted in a next step S14.

According to FIG. 1b, the alarm generation signal may preferably be an alarm generation signal ALS1 to an optical and/or acoustic output unit AE. The alarm generation signal ALS1 is consequently a control signal, which indicates a request to output an optical and/or acoustic warning by one or more output units AE.

The processor unit P can preferably send an alarm generation signal ALS2 in the form of a data message DN via the network interface N to additional network units. Additional network units are consequently informed hereby that an alarm generation state was detected at the medical device MV2.

Coming back to FIG. 4b, it can be embodied, for example, that, for example, the predefined value VWX is a threshold value. The processor unit P of the device MV2 from FIG. 1b is configured to determine at least one parameter value of the physiological parameter of the patient P on the basis of the sensor signal SIG and further to perform the detection of the alarm generation state in step S13 as a function of the parameter value and of the threshold value VWX. Consequently, if, for example, the parameter value of the physiological parameter determined on the basis of the sensor signal SIG exceeds the threshold value VWX, the alarm generation state is then detected and the process is branched off to step S14.

It is possible, as an alternative, that the predefined value VWX indicates a request on whether or not the detection of the alarm generation state shall be performed, so that the processor unit of the medical device MV2 performs the detection of the alarm generation state in step S13 as a function of the predefined value VWX.

The predefined value may be, for example, a Boolean variable, which indicates whether the detection of the alarm generation state shall be performed or whether it shall not be performed at all. If the predefined value VWX indicates that no detection of an alarm generation state shall be performed, the process branches off from step S13 to the right, so that no alarm generation state is detected.

If, however, the predefined value VWX indicates that a detection of the alarm generation state shall indeed be performed, a detection of an alarm generation state can still be performed, for example, by taking into consideration a threshold value predefined by the medical device MV2 itself and as a function of the sensor signal SIG.

This embodiment of the present invention makes it consequently possible that a so-called alarm suppression can be controlled from the outside via the network at the medical device MV2.

Figure 5A:
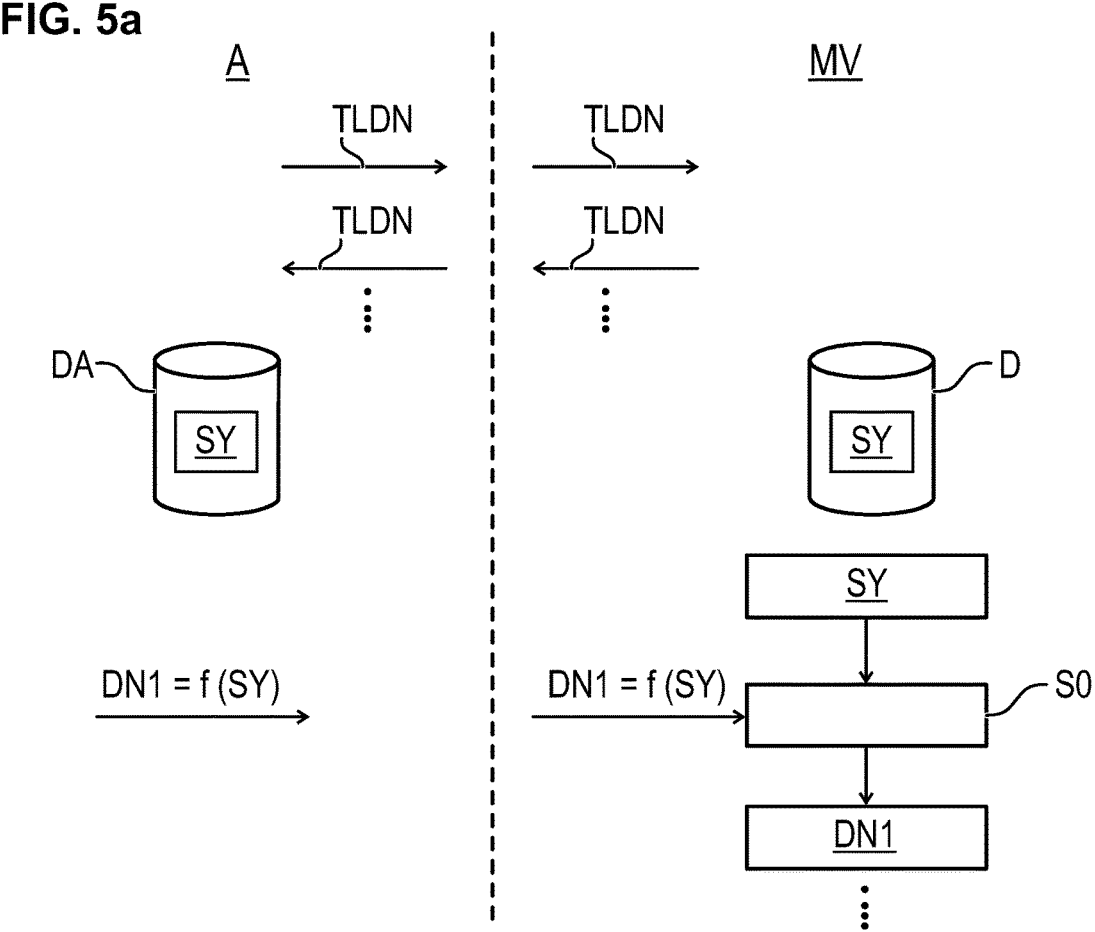
FIG. 5a is a view showing an exchange of data messages for an SSL or TLS handshake.

FIG. 5a shows an exchange of data messages TLDN between the sender A and the medical device MV, which may be the device MV1 from FIG. 1a or the device MV2 from FIG. 1b.

An exchange of data messages TLDN takes place here for performing a so-called handshake in order to make possible an agreement about a symmetrical key SY for an encrypted data transmission between the sender A and the device MV. After performing the handshake, preferably an SSL or TLS handshake, by means of the data messages TLDN, a symmetrical key SY is present both in the memory DA of the sender A and in the memory D of the device MV.

An alternative to carrying out the SSL or TSL handshake is an exchange of handshake messages according to the Diffie-Hellman method. The processor unit can then exchange the handshake messages with the sender via the network interface according to the Diffie-Hellman method in order to successfully reach the agreement with the sender about the symmetrical key, and finally to apply the symmetrical key to the data message after successful agreement.

The memory unit SP of the device MV provides a private key and a public key of the device MV. The memory unit SP further provides a so-called certificate. Such a certificate contains the public key of the device MV as well as a signature of a trustworthy, central certification unit. The sender A likewise provides a private key and a public key of his own as well as preferably a certificate by means of a memory unit of his own.

The device MV attempts to bring about an agreement with the sender about a symmetrical key SY by means of an exchange of the handshake messages TLDN.

If this agreement about the symmetrical key SY is successful, the device MV applies this symmetrical key SY at least to the first data message DN1 and preferably to additional, subsequent data messages.

The exchange of the certificate of the sender A to the device MV and preferably also the exchange of the certificate of the device MV to the sender preferably take place within the framework of the handshake.

The device MV can then check the received certificate of the sender A on the basis of the public key of the sender. This public key is transmitted in the course of the exchange of the handshake messages TLDN from the sender A to the device MV, which then receives this.

The exchange of the handshake messages TLDN from FIG. 5a preferably contains a so-called "keep-alive" request by the device MV and/or by the sender A. If the device MV and the sender have agreed upon the "keep-alive" functionality, the processor unit P of the device MV monitors by means of a timer function a so-called time-out, on the basis of which a maximum time window, within which messages encrypted with the symmetrical key SY, for example, an encrypted data message DN1, must be received at the device MV, is monitored. The so-called tunnel function, which is made possible by the symmetrical key SY, is maintained only if a correspondingly symmetrically encrypted data message is received during the time-out or the corresponding time window. If the time-out or the time window comes to an end without such a symmetrically encrypted data message having been received, the device MV terminates the tunnel function or the encrypted transmission on the basis of the symmetrical key SY.

Data messages transmitted on the basis of the symmetrical key SY, for example, the data message DN1, now preferably carry in a header a data element, which indicates that the corresponding data message DN1 is encrypted by means of the symmetrical key SY. As a result, the receiving device MV can deduce that the symmetrical key SY is to be applied to the corresponding data message DN1.

The handshake by means of the data messages TLDN, which is shown here, is preferably performed before the steps of the method embodiments according to FIG. 4a or FIG. 4b are carried out.

The data message DN1 may thus consequently be, according to FIG. 5a, an encrypted message or a function of the symmetrical key SY. The data message DN1 can then be decrypted by the medical device MV by providing the key SY from the memory or data element D of the device MV in advance in a step S0 into the data message DN1, before the further steps of the preferred embodiments of the methods according to FIGS. 4a and 4b can take place.

This embodiment is especially advantageous because an encrypted transmission of the data messages guarantees data safety in the network and since the symmetrical encryption of the data messages requires a smaller amount of computing than an encrypted transmission by means of a so-called asymmetric encryption.

Figure 5B:
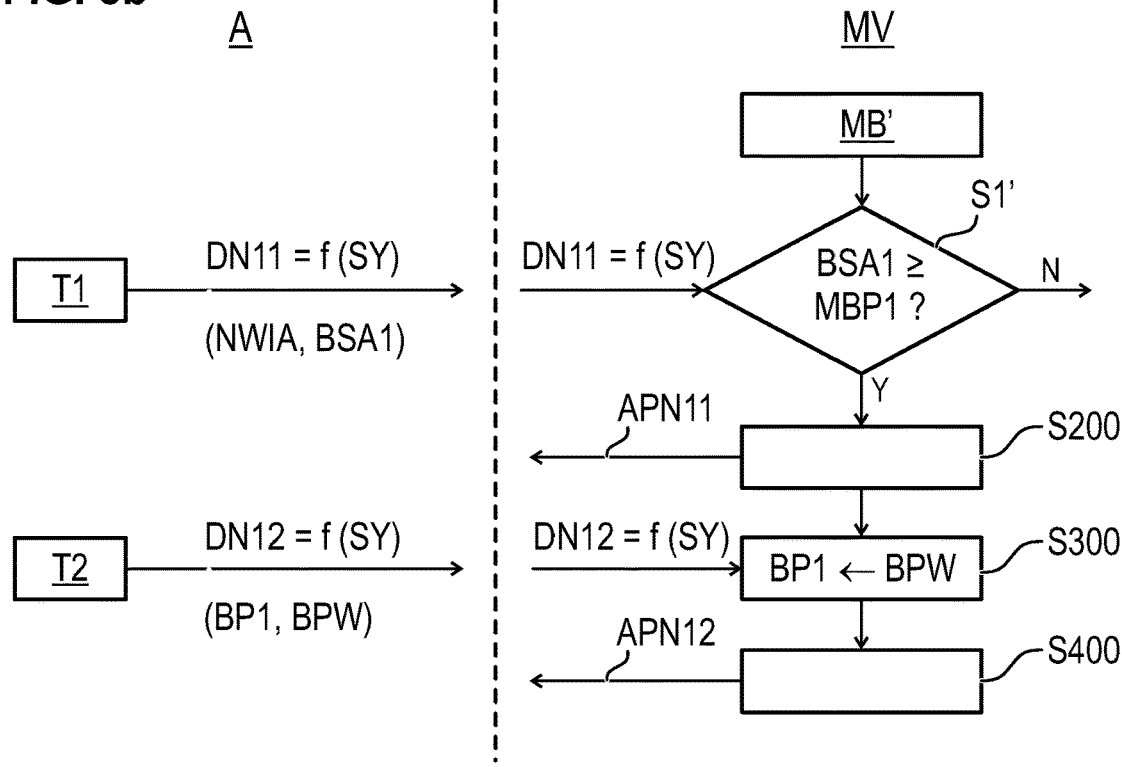
FIG. 5b is a view showing an exchange of data messages with the use of a data key.

According to FIG. 5b, the transmission of the data message DN1 from FIG. 5a may take place by means of sending a plurality of partial data messages DN11, DN12 at different times T1, T2.

If both the sender A and the medical device MV have the symmetrical key SY, the network identity NWIA of the sender A and also the authorization level BSA1 of the sender A can be transmitted in a first, encrypted partial data message DN11. After decrypting the partial data message DN11, the authorization level check is then performed first relative to the minimum authorization level MBP1 in a step S1', which is an alternative to step S1 according to FIG. 4a, and a confirmation message APN11 is sent to the sender A in a next step S200 in case of a successful calculation check or of a positive result of the determination.

A partial data message DN12, which does not necessarily have to have the network identity NWIA of the sender A any longer, but in which it is sufficient that only the requested operating parameter BP1 or operating parameter value BPW be indicated, can then be sent at a later time T2 by the sender A to the medical device MV.

If the medical device MV then receives this encrypted message, which is preferably encrypted with the symmetrical key SY, a repeated authorization check of the sender A can be eliminated after decrypting this partial data message DN12, so that the operating parameter BP1 is set directly to the requested value BPW in a step S300.

A confirmation message APN12 is then preferably sent to the sender A in a step S400.

Such a division of the data message DN1 from FIG. 5a into partial data messages DN11 as well as DN12 in case of an encrypted transmission with a symmetrical key can also be applied to the data message DN1' according to FIG. 4b.

Figure 6A:
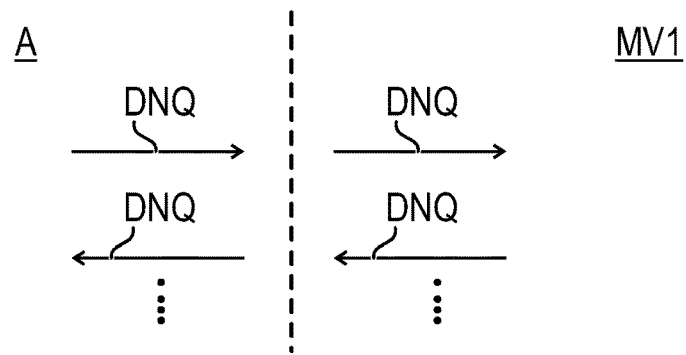
FIG. 6a is a view showing an exchange of data messages to determine a data transmission quality.

FIG. 6a shows an exchange of data messages DNQ to determine a data transmission quality between the sender A and the medical device MV1.

Corresponding data messages DNQ can now be exchanged to determine a data transmission quality between the sender A and the device MV1.

For example, a latency measurement of the data transmission between the two network computers can be carried out hereby. As an alternative or in addition, a bit error rate of the data transmission between these network computers can be determined.

As an alternative or in addition, a consistency check of the requested predefined value can preferably be performed by a data message, which indicates or predefines the predefined value, further also indicates or shows the current value that the operating parameter shall have prior to the use of the predefined value. The medical device can then check whether the request is consistent, because it is only in the case in which the operating parameter does indeed currently have the current value indicated in the data message that the device sending the data message also assumes a correct current value of the operating parameter.

Figure 6B:
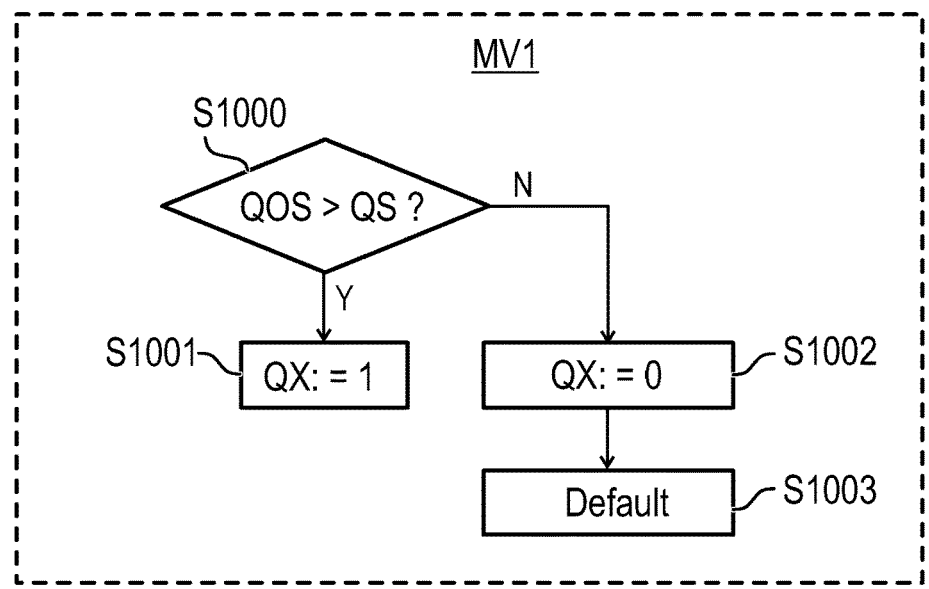
FIG. 6b is a view showing an embodiment of a step in which a data transmission quality is taken into consideration.

According to FIG. 6b, a data transmission quality QOS determined on the basis of the data message DNQ is used in a later step S1000 to change the operating parameter as a function of the result of the determination and the data transmission quality QOS and/or to perform the detection of the alarm generation state.

The transmission quality QOS determined on the basis of the data messages DNQ is compared to this end in a step S1000, for example, with a threshold value QS. If the data transmission quality QOS is sufficient, the process is branched off to a step S1001, in which, for example, a data element QX is set to the value 1.

If the data transmission quality is not sufficient, the process is branched off, for example, to a step S1002, in which, for example, the data element QX is set to the value 0.

If the data transmission quality is not sufficient, the medical device MV1 is put into a so-called basic state or basic operating parameter in a step S1003. These are, for example, a predefined ventilation mode, for example, in the case of a ventilator. The medical device as a ventilator assumes this because a minimum supply of the patient is thus guaranteed.

Figure 6C:
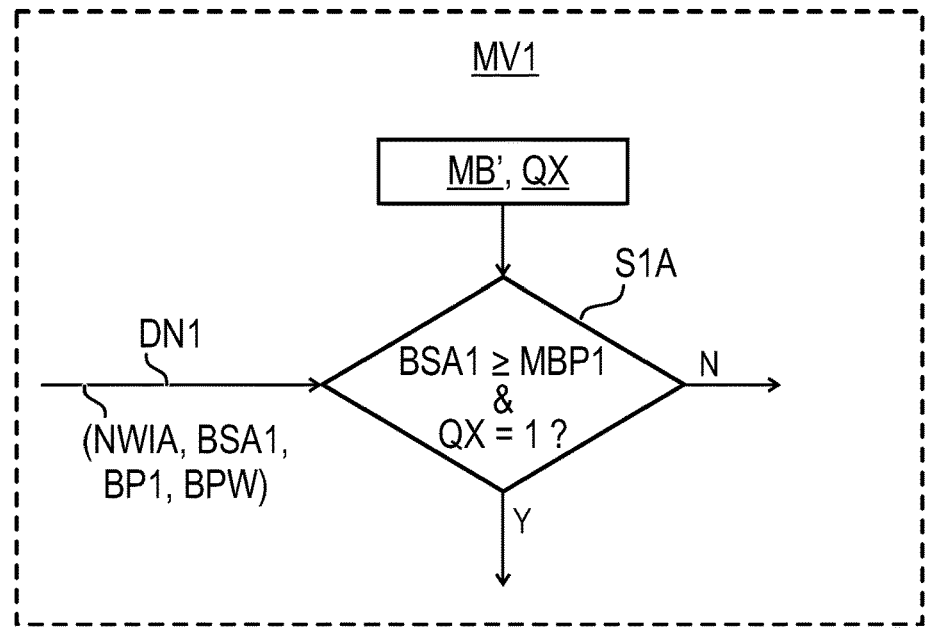
FIG. 6c is a view showing another embodiment of a step in which a data transmission quality is taken into consideration.

FIG. 6c shows an alternative step S1A to step S1 in FIG. 4a.

The data quality is also taken into consideration in this case in the form of the quality element QX in order to make a dependence of a change in an operating parameter contingent upon the data transmission quality.

A change is actually also made in the operating parameter BP1, which parameter is indicated in the data message DN1, only if the data transmission quality is sufficient, which is given here by the data element QX=1.

Such a step S1A according to FIG. 6c as an alternative to step S1 in FIG. 4a may analogously also be provided for the step S10 for predefining a predefined value VWX.

This is likewise possible in connection with the encryption of the data messages DN1 as well as with a division of a data message DN1 into partial data messages DN11, DN12, as was described above according to FIG. 5b.

Figure 7:
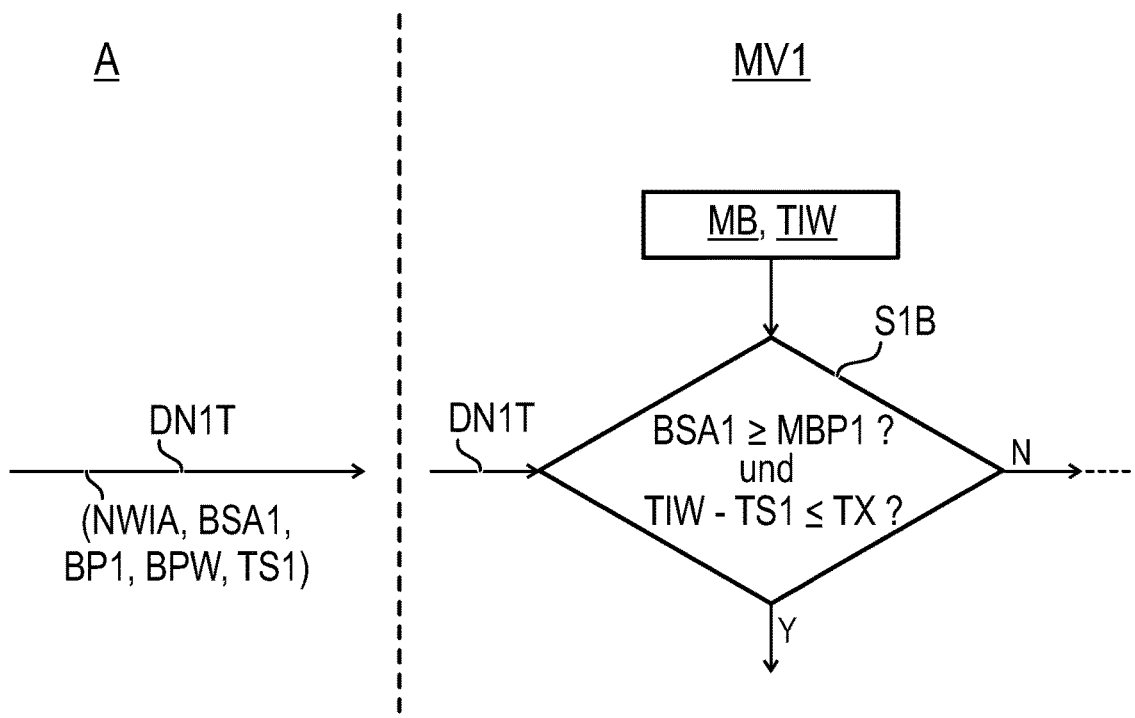
FIG. 7 is a view showing an embodiment of a step in which a time stamp is taken into consideration.

FIG. 7 shows a preferred embodiment, in which the data message DN1T further has a time stamp TS1, which is taken into consideration in an alternative step S1B. The alternative step S1B is an alternative to the step S1 according to FIG. 1a.

A current time value TIW of the timer function TI of the processor P according to FIG. 1a is taken into consideration in step S1B.

If a deviation TIW-TS1 between the current time value TIW and the time stamp TS1 is greater than a predefined threshold value TX, the authorization check takes place in step S1B and the result of the determination is negative (N).

The result of the determination can only be positive (Y) if this time difference is smaller than the time threshold value TX.

The operating parameter BP1, which is indicated in the data message DN1T, is consequently changed as a function of the result of the determination and of the time stamp TS1.

As an alternative, the detection of the alarm generation state may be performed as a function of the time stamp.

Alternative embodiments may be configured for this, in which the alternative step S1B is adapted instead of step S10 according to FIG. 4b for the example of the changing of a predefined value.

Corresponding embodiments may also be configured for an encryption of the data message DN1T, as is proposed according to FIG. 5a by means of a symmetrical key SY. It is likewise possible to derive embodiments in which the data message DN1T according to FIG. 7 is divided into partial data messages, as was explained above with reference to FIG. 5b.

Even though some aspects were described in connection with a device, it is obvious that these aspects also represent a description of the corresponding method, so that a block of a block diagram or a component of a device may also be defined as a corresponding method step or as a feature of a method step. Analogously to this, aspects that were described in connection with a method step or as a method step also represent a description of a corresponding block of a block diagram or details or features of a corresponding device.

Depending on certain implementation requirements, exemplary embodiments of the present invention may be implemented in hardware or in software. The implementation may be executed with the use of a digital storage medium, for example, a floppy disk, a DVD, a Blu-Ray disk, a CD, a ROM, a PROM, an EPROM, an EEPROM or a flash memory, a hard drive or another magnetic or optical storage device, on which electronically readable control signals, which can interact or do interact with a programmable hardware component such that the particular method is executed, are stored.

A programmable hardware component may be formed by a processor, a computer processor (CPU=Central Processing Unit), a graphics processor (GPU=Graphics Processing Unit), a computer, a computer system, an application-specific integrated circuit (ASIC=Application-Specific Integrated Circuit), an integrated circuit (IC=Integrated circuit), a single-chip system (SOC=System on Chip), a programmable logic component or a field-programmable gate array with a microprocessor (FPGA=Field Programmable Gate Array) and combinations thereof.

The digital storage medium may therefore be machine- or computer-readable.

Some exemplary embodiments consequently comprise a data storage medium, which has electronically readable control signals, which are capable of interacting with a programmable computer system or with a programmable hardware component such that one of the methods being described here is executed. One exemplary embodiment is consequently a data storage medium (or a digital storage medium or a computer-readable medium), on which the program for executing one of the methods being described here is recorded.

Exemplary embodiments of the present invention may generally be implemented as program, firmware, computer program or computer program product with a program code or as data, wherein the program code or the data act in such a way as to execute one of the methods when the program is running on a processor or on a programmable hardware component. The program code or the data may also be stored, for example, on a machine-readable storage medium or data storage medium. The program code or the data may be, among other things, in the form of source code, machine code or byte code as well as as other intermediate code.

While specific embodiments of the invention have been shown and described in detail to illustrate the application of the principles of the invention, it will be understood that the invention may be embodied otherwise without departing from such principles.

What is claimed is:

1. A medical device comprising:
   a sensor interface for detecting a sensor signal, which indicates a physiological parameter of a patient;
   a network interface configured to receive at least one data message, which indicates a network identity of a sender of the at least one data message, which indicates at least one authorization level of the sender of the at least one data message, and which indicates a request of the sender to change a set alarm detection predefined threshold value for an alarm detection to a changed alarm detection predefined threshold value by indicating an alarm detection predetermined threshold value type and an alarm detection predetermined threshold value;
   a memory unit configured to provide one or more predefined minimum authorization level with a corresponding alarm detection predetermined threshold value type and the set alarm detection predefined threshold value;
   a processor unit configured:
   to receive the sensor signal and determine therefrom a parameter value of the physiological parameter of the patient on the basis of the signal;
   to determine an actual authorization of the sender to change the set alarm detection predefined threshold value on the basis of the authorization level of the sender and the alarm detection predetermined threshold value type from the at least one data message and on the basis of the predefined minimum authorization level and corresponding alarm detection predetermined threshold value type provided by the memory unit;
   as a function of the result of the determination of the actual authorization of the sender, to change the set alarm detection predefined threshold value of the memory to the alarm detection predefined threshold value indicated in the at least one data message; and
   to perform a detection of the alarm generation state as a function of the determined parameter value and as a function of the alarm detection predefined threshold value indicated in the at least one data message.

2. A medical device in accordance with claim 1, wherein:
   the predefined threshold value indicates a request as to whether or not the detection of the alarm generation state shall be performed as a function of the predefined threshold value; and
   the processor unit is further configured to perform the detection of the alarm generation state as a function of the predefined threshold value.

3. A medical device in accordance with claim 1, wherein the data message is an encrypted data message.

4. A medical device in accordance with claim 1, wherein:
   the processor unit is further configured to exchange handshake messages with the sender via the network interface in order to successfully reach an agreement with the sender about a symmetrical key;
   and to apply the symmetrical key to the data message after successful agreement.

5. A medical device in accordance with claim 4, wherein:
   the memory unit is further configured to provide a private key and a public key;
   the processor unit is further configured:
   to exchange the handshake messages with the sender on the basis of the private key and the public key via the network interface in order to successfully reach an agreement with the sender about the symmetrical key; and
   to apply the symmetrical key to the data message after successful agreement.

6. A medical device in accordance with claim 4, wherein the processor unit is further configured to:
   exchange the handshake messages with the sender via the network interface according to the Diffie-Hellman method to successfully reach agreement with the sender about the symmetrical key; and
   to apply the symmetrical key to the data message after successful agreement.

7. A medical device in accordance with claim 1, wherein the processor unit is further configured to:
   exchange data messages via the network interface to determine a data transmission quality between the sender and the medical device; and
   to change the actuator operating parameter and/or to perform the detection of the alarm generation state as a function of the result of the determination and the determined data exchange quality.

8. A medical device in accordance with claim 1, wherein:
   the data message further has a time stamp; and
   the processor unit is configured to perform the detection of the alarm generation state as a function of the result of the determination and the time stamp.

9. A medical device in accordance with claim 1, further comprising an actuator for physiologically acting on a patient connected to the medical device, wherein:
   the network interface is configured to receive at least one other data message, which other data message indicates a network identity of a sender of the message, and at least one actuator authorization level of the sender, and a request of the sender to change a set actuator operating parameter of the actuator to a changed actuator operating parameter by indicating an actuator operating parameter type and an actuator operating parameter;

the memory unit is configured to hold the set actuator operating parameter and provide an actuator operating parameter authorization level and a corresponding actuator operating parameter type; and the processor unit is configured:

to determine an actual actuator authorization of the sender, of the at least one other data message with the request to change an actuator operating parameter, to change the actuator operating parameter on the basis of the authorization level of the sender and the actuator operating parameter type of the at least one other data message with the request to change an actuator operating parameter and on the basis of the actuator operating parameter authorization level and corresponding operating parameter type provided by the memory; and as a function of the result of the determination, to change the set actuator operating parameter to the actuator operating parameter indicated in the at least one other data message.

10. A medical device in accordance with claim 9, wherein the processor unit is further configured to:

exchange data messages via the network interface to determine a data transmission quality between the sender and the medical device;

to change the actuator operating parameter as a function of the result of the determination and the determined data exchange quality.

11. A medical device in accordance with claim 9, wherein: the data message further has a time stamp; and the processor unit is configured to change the actuator operating parameter as a function of the result of the determination and the time stamp.

12. A method for operating a medical device, wherein the medical device comprises a network interface, a processor unit and a memory unit, a sensor interface for detecting a sensor signal, which sensor signal indicates a physiological parameter of a patient, the method comprising the steps of:

receiving, via the network interface, at least one data message, which indicates a network identity of a sender of the at least one data message, which indicates at least one authorization level of the sender of the at least one data message and which indicates a request of the sender to change a set alarm detection predefined threshold value for an alarm detection to a changed alarm detection predefined threshold value by indicating an alarm detection predetermined threshold value type and an alarm detection predetermined threshold value;

providing, via the memory unit at the medical device, a predefined minimum authorization level with a corresponding alarm detection predetermined threshold value type and a set alarm detection predefined threshold value;

with the processor unit, receiving the sensor signal and determining therefrom a parameter value of the physiological parameter of the patient on the basis of the signal;

determining, an actual authorization of the sender to change the set alarm detection predefined threshold value on the basis of the authorization level of the sender and the alarm detection predetermined threshold value type from the at least one data message and on the basis of the predefined minimum authorization level and corresponding alarm detection predetermined threshold value type provided by the memory;

as a function of the result of the determination of the actual authorization of the sender and with the processor unit changing the set alarm detection predefined threshold value to the alarm detection predefined threshold value indicated in the at least one data message; and with the processor unit, detecting an alarm generation state as a function of the determined parameter value and as a function of the alarm detection predefined threshold value indicated in the at least one data message.

13. A method in accordance with claim 12, wherein:

the medical device further comprises an actuator for physiologically acting on a patient connected to the device;

at least one other data message is received which indicates a network identity of a sender of the data message, at least one actuator authorization level of the sender as well as a request of the sender to change a set actuator operating parameter of the actuator to a changed actuator operating parameter by indicating an actuator operating parameter type and an actuator operating parameter;

the memory unit is configured to hold a set actuator operating parameter and provide an actuator operating parameter authorization level and a corresponding actuator operating parameter type;

the processor unit determines an actual actuator authorization of the sender, of the at least one data message with the request to change an actuator operating parameter, to change the actuator operating parameter on the basis of the predefined minimum authorization level of the sender and the actuator operating parameter type of the at least one other data message with the request to change an actuator operating parameter and on the basis of the actuator operating parameter authorization level and corresponding operating parameter type provided by the memory;

as a function of the result of the determination and with the processor unit changing the set actuator operating parameter to the actuator operating parameter indicated in the at least one other data message.

14. A medical device in accordance with claim 9, wherein the network interface is configured to receive a single data message comprising both:

the at least one data message; and the at least one other data message.

15. A medical device in accordance with claim 9, wherein the network interface is configured to receive both the at least one data message, as separate messages wherein the sender of the messages is the same sender or different senders.

16. A method in accordance with claim 13, wherein the network interface is configured to receive a single data message comprising both:

the at least one data message; and the at least one other data message.

17. A method in accordance with claim 13, wherein the network interface is configured to receive both the at least one data message, as separate messages wherein the sender of the messages is the same sender or different senders.

* * * * *